United States Patent [19]
Bonnet et al.

[11] Patent Number: 5,461,059
[45] Date of Patent: Oct. 24, 1995

[54] DERIVATIVES OF TERBUTYLPHENYL-1-AMINO-4-HYDROXYBUTANE THEIR PREPARATION PROCESSES AND THE PHARMACEUTICAL COMPOSITIONS CONTAINING THEM

[75] Inventors: Paule Bonnet, Menton; Remi Delansorne, Nice; Maurice Faure, Eze; Michel Languetin, La Trinite; Serge Zunino, Beaulieu, all of France

[73] Assignee: Laboratoire Theramex S.A., France

[21] Appl. No.: 861,816

[22] PCT Filed: Oct. 17, 1991

[86] PCT No.: PCT/FR91/00811

§ 371 Date: Feb. 8, 1993

§ 102(e) Date: Feb. 8, 1993

[87] PCT Pub. No.: WO92/06977

PCT Pub. Date: Apr. 30, 1992

[30] Foreign Application Priority Data

Oct. 17, 1990 [FR] France .................... 90 12562

[51] Int. Cl.⁶ .................. C07D 401/12; C07D 247/02; C07D 473/08
[52] U.S. Cl. ................ 514/265; 514/322; 544/271; 544/272; 544/370; 546/199
[58] Field of Search .................... 544/271, 272, 544/370; 546/199; 514/265, 322

[56] References Cited

U.S. PATENT DOCUMENTS

| | | | |
|---|---|---|---|
| 3,161,645 | 12/1964 | Janssen | 260/293.4 |
| 4,219,559 | 8/1980 | Janssens | 424/267 |
| 4,430,343 | 2/1984 | Iemura | 544/370 |
| 4,908,372 | 3/1990 | Carr | 514/322 |
| 5,278,165 | 1/1994 | Janssens | 544/272 |

OTHER PUBLICATIONS

Janssens, J. Med. Chem. 28, 1925 (1985).

Primary Examiner—Mark L. Berch
Attorney, Agent, or Firm—Bierman and Muserlian

[57] ABSTRACT

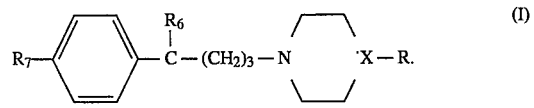

The present invention concerns (4-substituted phenyl)4-oxy 1-aminobutane of the general formula (I) in which X is a nitrogen atom or >CH—CH, and R is a cyclic substituent chosen from the group comprising a) a xanthic substituent, b) a benzimidazolic substituent, as well as salts and optic isomers of the compounds of formula (I). The invention also concerns processes for obtaining the compounds of formula (I) and pharmaceutical compositions containing, as antihistamine ingredient, at least one compound of formula (I) or one of its salts with a mineral or organic acid.

13 Claims, No Drawings

DERIVATIVES OF TERBUTYLPHENYL-1-AMINO-4-HYDROXYBUTANE THEIR PREPARATION PROCESSES AND THE PHARMACEUTICAL COMPOSITIONS CONTAINING THEM

This invention relates to novel derivatives of phenyloxy butanes carrying in position 1 an amino group, the processes for their production and the pharmaceutical compositions containing them as active ingredients.

The present invention more particularly relates to novel derivatives of phenyl butane, the butane side-chain of them carrying in position 1 an amino cyclic chain.

This invention specifically relates to novel derivatives of 4-($R_7$-phenyl) 4-oxy 1-aminobutanes of general formula I

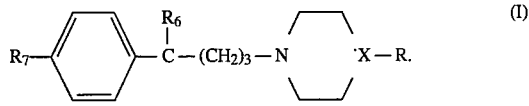

wherein
—$R_6$ is selected from the group consisting of HOH, =O and

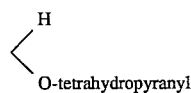

X is a substituent selected from the group consisting of >N— and >CH—NH $R_7$ represents COOH, tertbutyl or

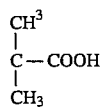

and

R is a cyclic substituent selected from the group consisting of
a) a xanthic derivative of the formula

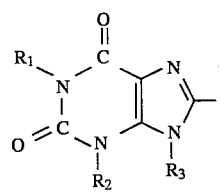

wherein
$R_1$ and $R_2$, the same or different, are a hydrogen or a lower alkyl radical having from 1 to 5 carbon atoms in straight or branched chain and
$R_3$ is a halogenated derivative selected from the group consisting of a halogenbenzyl group of the formula

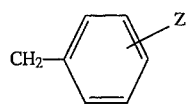

wherein
Z is a halogen atom and an ethoxyethyl radical ($CH_2CH_2OC_2H_5$) and b) a benzimidazolic derivative of general formula

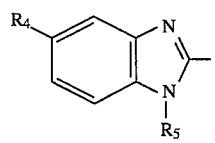

wherein
$R_4$ is a hydrogen or a halogen atom and
$R_5$ is a halogenobenzyl group

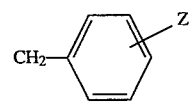

wherein Z is a halogen or an ethoxyethyl radical.

Among the compounds of general formula I it may then be cited the two following sub-groups:

1. the compounds of general formula $I_A$ wherein R is a xanthyl group, selected from the group consisting of piperazinyl xanthines of general formula $I_{A'}$

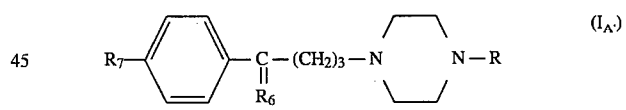

wherein R is xanthyl group define as previously and the piperidyl amino xanthines of general formula $I_{A''}$

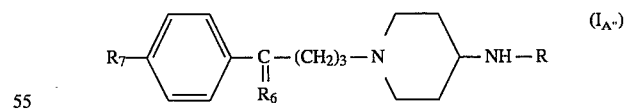

wherein R is a xanthyl group defined as previously.

2. the compounds of general formula $I_B$ wherein R is a benzimidazolic group selected from the group consisting of piperazinyl benzimidazoles of general formula $I_{B'}$

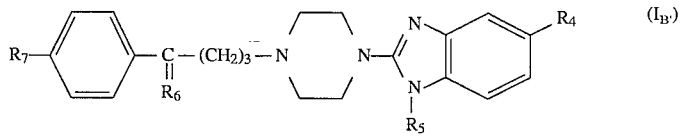

wherein $R_4$, $R_5$, $R_6$ and $R_7$ have the above-given definitions and the piperidylamino benzimidazoles of formula $I_{B'''}$

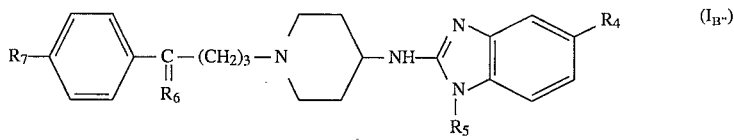

wherein $R_4$, $R_5$, $R_6$ and $R_7$ are defined as previously given.

Among those compounds of formula I, the most preferred ones are those for which $R_7$ is a tertbutyl radical and namely the compounds of general formula $I_B$ wherein R is a benzimidazolic group such as the piperazinyl benzimidazoles of formula $I_{B'}$

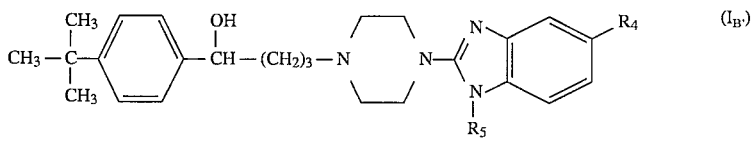

wherein $R_4$ and $R_5$ are defined as previously-indicated and the piperazinyl benzimidazoles of formula $I_{B''}$

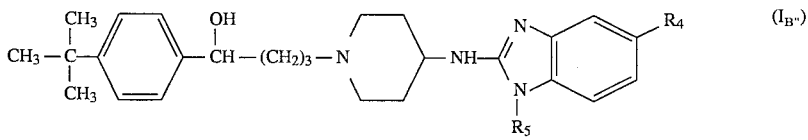

wherein $R_4$ and $R_5$ have the previously-given definition. Generally-speaking the presently preferred compounds are further those for which $R_5$ is a fluorobenzyl radical and $R_6$ is a hydroxy radical.

This invention also relates to the acid addition salts of a compound of formula I with a mineral or organic acid, preferably a therapeutically-compatible acid.

Those which cannot be used in therapy, such as the iodates, periodates, reineckates or picrates, are utilized as a mean for isolating, purifying or characterizing these compounds.

Moreover the compounds of general formula I include at least one asymmetric carbon and consequently may be resolved into their optical isomers, namely by salification using a chiral acid such as d-camphosulphonic acid, d-dibenzoyltartaric acid, NN-diethyl d-tartramic acid or d-glucose 1-phosphoric acid.

The compounds of general formula I may also be resolved into their optically-active isomers by acylating first by means of an optically-active acid such as 1-methoxy acetic then with mild saponification. It is further possible to resolve these esters by enzymatic hydrolysis or through chromatography on a column loaded with a chiral absorbant.

The present invention further relates to a process for producing the compounds of formula I which consists in that for the xanthic derivatives of formula I, a halogeno xanthine having the formula II

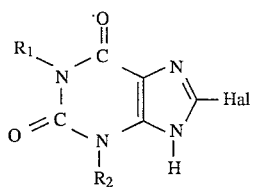

wherein
$R_1$ and $R_2$ are defined as previously given and
Hal is a chlorine or bromine
is let to react with a halogenated derivative selected from the group consisting of a benzylic halide having the formula III

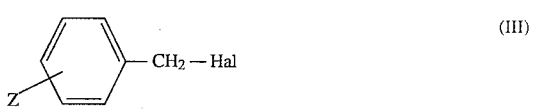

and an ethoxyethyl halide of formula III'

wherein

Hal means a chlorine or bromine, and

Z is a halogen atom to obtain a xanthic derivative of general formula IV

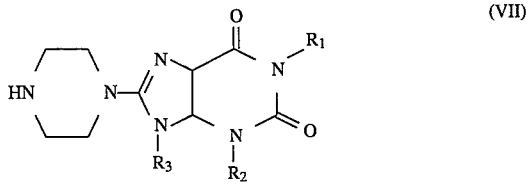

wherein $R_1$, $R_2$, $R_3$ have the above-given definitions.

This reaction is preferably performed in a solvent selected from the cyclic ethers and the alkanols having up to 3 carbon atoms in straight or branched chain, at the reflux temperature of the selected solvent (ether or alkanol) for 2 to 12 hours. A compound of formula $I_{A'}$ is thus obtained

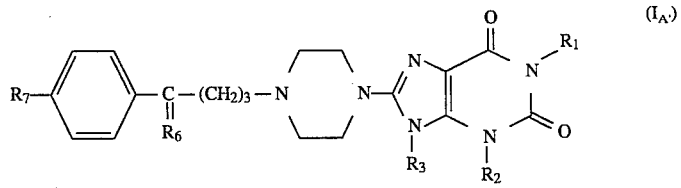

(I$_{A'}$)

wherein $R_1$, $R_2$, $R_3$, $R_6$ and $R_7$ have the above-given definitions.

When X is equal to >CH—NH—, the corresponding compound of formula V is prepared by condensing a derivative of general formula VI defined as previously with a 4-oximino piperidine of formula VIII

(VIII)

This reaction preferably is carried out in a solvent selected among the alkanols having up to 3 carbon atoms in straight or branched chain, in the presence of an alkaline agent such as an alkali metal carbonate, at the reflux temperature of the selected alkanol, for 8 to 12 hours.

A derivative of formula IX is thus obtained

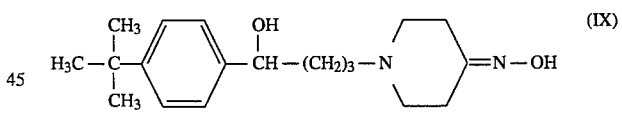

(IX)

wherein $R_6$ is a hydroxyl and $R_7$ has the above-given meanings.

The oximino derivative IX is further reduced into a primary amine in a medium consisting of an alkanol having up to 3 carbon atoms in straight or branched chain, by means of an alkali metal at a temperature selected from 20° and the reflux temperature of the alkanol, during from 2 to 12 hours depending on the used temperature.

The aminated derivative of formula X is thus obtained

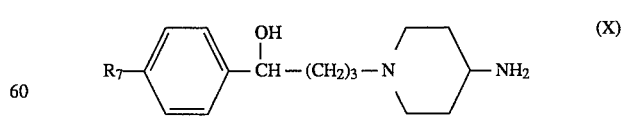

(X)

wherein $R_7$ has the above-given definition which is condensed with a compound of general formula IV to produce a compound of formula $I_{A''}$

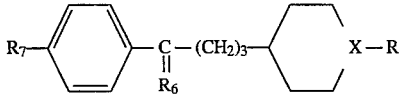

(IV)

wherein $R_1$, $R_2$ and $R_5$ are defined as previously-given then reacts the latter with a 4-(4-$R_7$-phenyl) 4-oxy 1-aminobutyl derivative of general formula V (V)

wherein

X, is defined as above-given $R_6$ and $R_7$ have the above-given definitions and R is a xanthyl group to produce a compound of formula $I_{A''}$.

When X is equal to >N— and R to xanthyl, the compound of formula $I_{A'}$ may further be produced by condensing a 4-halogeno 1-($R_7$-phenyl)butyl derivative of general formula VI

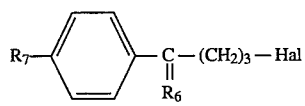

(VI)

wherein $R_6$ and $R_7$ have the above-given definitions and

Hal is a bromine or chlorine with a N-Xanthyl piperzine of formula VII

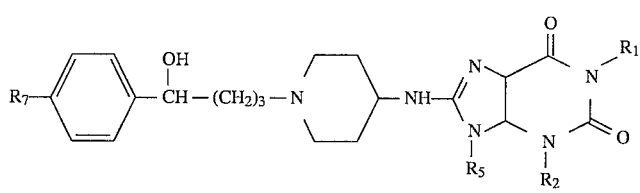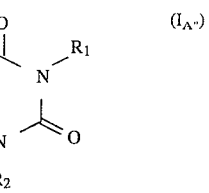

(I_A″)

wherein $R_1$, $R_2$, $R_5$ and $R_7$ have the above-given definitions.

This reaction is preferably performed in a solvent selected from the alkanols having from 1 to 5 carbon atoms in straight or branched chain and the polar solvents in the presence of an alkaline agent, an alkali metal carbonate, an earth-alkali metal carbonate, and in the presence of a catalyst such as an alkali-metal iodide. The carbonates may be those of calcium, sodium or potassium. The reaction is carried out at the reflux of the selected solvent, for a set of time which may range from 4 to 30 hours depending on the experimental conditions.

They are thus obtained the derivatives of general formula $I_A$ wherein the cyclic amino group is a Xanthyl piperidyl amino or piperazinyl grouping. They may be further converted into the corresponding ketones ($R_6$=O) by means of a metallic oxydizing agent.

These new compounds corresponding to the general formula $I_{A'}$ and $I_{A''}$ which have thus been produced, may be salified by adding a mineral or organic acid, preferably a therapeutically-compatible acid, to obtain the corresponding acid addition salts. These salts also are part of the present invention.

Mainly as acids which may be used for forming the acid addition salts, it may be cited as an example, the hydrochloric, hydrobromic, sulphuric, phosphoric, acetic, propionic, maleic, fumaric, citric, benzoic and metane sulphonic acids.

These new compounds of general formula $I_A$ are purified, when and if necessary, by means of physical or chemical methods such as by recrystallization or by chromatography.

These compounds have been identified and controlled for the purpose of pharmacological studies, by means of known analysis methods such as elementary analysis, infra-red spectrophotometry, ultra-violet spectrophotometry, Nuclear Magnetic Resonance (NMR), or high performance liquid chromatography (HPLC).

When R is a benzimidazolyl group, the compounds of general formula I in which R is the said benzimidazolyl group and X is an amino >N— group, are produced by condensing an halogenated benzimidazole of general formula XI

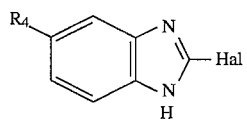

(XI)

wherein $R_4$ is defined as above-given and

Hal means a chlorine or bromine atom with a halogenated derivative selected from the group consisting of benzylic derivative of formula III

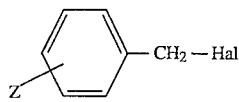

(III)

and ethoxyethyl halides of formula III'

$CH_3CH_2OCH_2CH_2$ Hal wherein

Hal means a chlorine or bromine and

Z is a halogen atom to produce a halogenated benzimidazole having the general formula XII

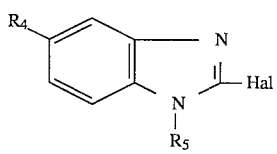

(XII)

wherein $R_4$ has the above-given definitions and particularly chlorine or hydrogen.

The compound of formula XII is reacted with piperazine in a medium consisting of a solvent selected among the aromatic hydrocarbons and the substituted aromatic hydrocarbons. The preferred solvents are benzene, toluene and the xylenes. It may be of advantage to perform the reaction at a temperature ranging between 40° C. and the boiling point of the solvent for set of time ranging from 4 to 24 hours, depending on the used temperature.

A benzimidazolic derivative of general formula XIII is thus produced

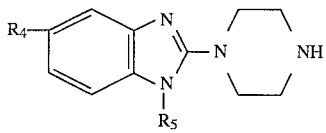

(XIII)

wherein

—$R_4$ means hydrogen or chlorine and $R_5$ has the previously-given meanings which is reacted with a 4-halogeno 1-(4-$R_7$-phenyl)butane of formula VI

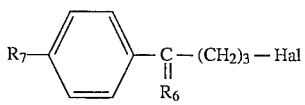

(VI)

wherein

Hal means a chlorine or bromine and $R_6$ and $R_7$ have the above-given definitions to produce a compound having the general formula $I_{B'}$

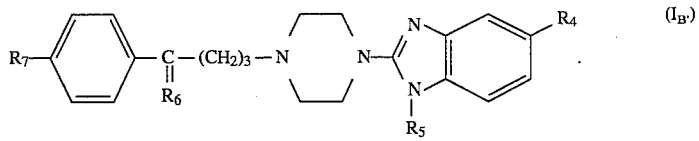

SCHEME OF SYNTHESIS FOR THE
BENZIMIDAZOLIC DERIVATIVES $I_B$ (X=>CH—NH and R=benzimidazolyl)

First Step

Compounds of general formula $I_{B''}$ are produced according to the method which consists in reacting a o.nitroaniline of formula

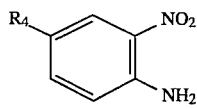

with a halogenated derivative selected from the group consisting of a halogenated benzylic derivative of formula III

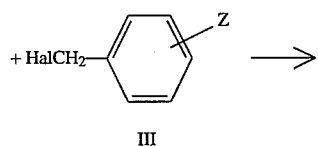

and ethoxyethyl halides of formula

Hal $CH_2CH_2OCH_2CH_3$ wherein
  Z has the above-given meaning and
  Hal is a chlorine or a bromine
to produce an o.nitroaniline of the formula III'

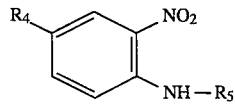

Second Step reducing the nitro o.phenylenediamine to produce the corresponding amine of formula XVI

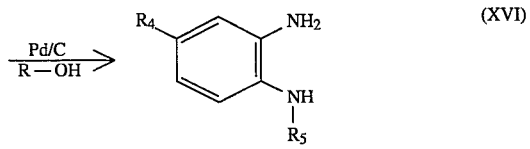

Third Step from a compound of formula X, a tetrahydropyranylated of derivative of formula XIV

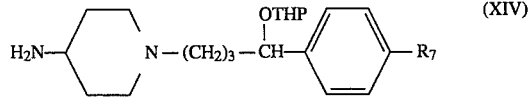

is prepared wherein the hydroxyl alcoholic function is blocked by the group tetrahydropyran.

Fourth Step formation of the thiocyanate of formula XV by action of carbon disulphide in sodic medium on the tetrahydropyranylated of derivative XIV

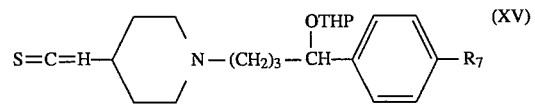

Fifth Step condensing the benzylamine of formula XVI with the thiocyanate of formula XV to produce a thiourea of formula XVII

-continued

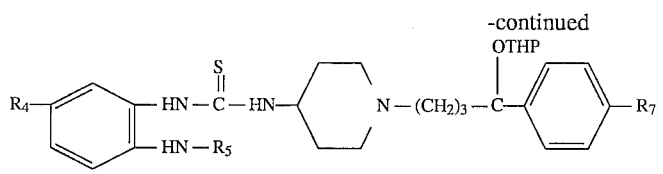

Sixth Step cyclizing in an aromatic hydrocarbon in the presence of a desulphurizing agent to produce a benzimidazolic derivative of formula XVIII

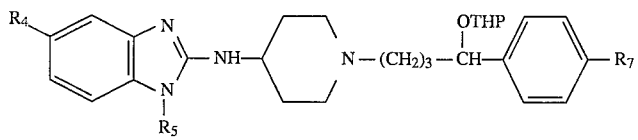

Second Step hydrolyzing in acidic medium the tetrahydropyranyl ether under very mild conditions to obtain a benzimidazolic derivative of formula $I_{B''}$ wherein $X=>C=NH$

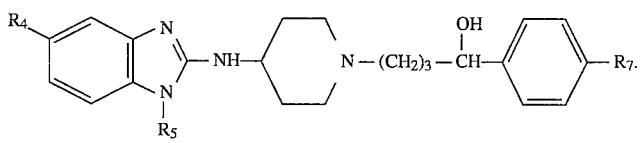

The compounds of general formula I which bear a benzimidazolic substituent, of general formula $I_B$ et $I_{B''}$, thus obtained, may be: metalic oxidizing reagent, or salified by adding a mineral or organic acid, or purified using the same methods as above for the xanthic deriviatives, or identified and controlled for the purpose of pharmacological studies, using the same techniques as previously described.

The compounds of formula I are endowed with interesting pharmacological properties, namely anti-histaminic and anti-allergic properties. Particularly the compounds of general formula $I_B$ in which R is a benzimidazole ring, and their acid addition salts with a mineral or organic, therapeutically-tolerable, acid, namely display anti-histaminic properties by action on the $H_1$-receptors which are of the same type than that encountered with ASTEMIZOLE.

The compounds of general formula I find hence a use in therapy, mainly in the allergic states and in the treatment of asthma.

This invention also relates to pharmaceutical compositions including as active ingredient one derivative of general formula I or a physiologically tolerable acid addition salt thereof, in admixture or conjunction with a suitable pharmaceutical carrier.

The thus produced pharmaceutical compositions are advantageously offered in the various forms suitable for the oral, way such as for example tablets, dragees, soft gelatine, capsules, or preparations suitable for the administration for the nasal, injectibles ophthalmic, drinkable ways as well as in the form of aerosol, or by rectal way.

The unit dosology may range from 1 to 20 mg per unit dosage. The daily dosage will vary between 1 and 100 mg in the adult man.

The following examples are given as an illustration of the invention and do not limit it.

The melting points—unless the contrary is mentioned—have been determined using a Mettler apparatus. The infra-red spectras are determined with a Perkin Elmer Spectrophotometer 1600 serial FTIR. The UV spectrums are measured using a Kontron spectrophotometer type UVIKON 860. The determination by HPLC have been performed with a Waters Apparatus type 600 E, fitted with an integrator APC 4.

EXAMPLE I 1,3-dimethyl 7-(4-fluorophenyl) 8-[1-(4-tertbutylphenyl) 4-hydroxybutyl 4-piperidyl amino] Xanthine ($I_A''$)

Step A: Hydroxyamino Piperidine 46.2 g of piperidine 4-one as the hydrochloride are heated at the reflux temperature under stirring with 38.4 g hydroylamine hydrochloride in 250 ml ethanol in the presence of 100 g sodium carbonate. After 3 hours reflux, the resulting suspension is filtered and the solid is washed four times with 100 ml boiling ethanol. The ethanolic solution is concentrated under vacuum. The solid residue is taken up in methylene chloride, filtered on a clay (Trade mark Celite®), and concentrated a new to dryness. 34.1 g of a colourless product are obtained which melts at 117.2° C. In TLC it is mono-spot in a system formed with methanol 100/ammonia 2, on plates of silica MERCK and staining with $CuCl_2$/ninhydrin.

Step B: 1-[4-tertbutyl phenyl) 4-hydroxy 1-butyl] 4-hydroxy iminopiperidine

A mixture of 11.4 g 4-oximinopiperidine of step A, 24 g of 4-chloro 4-(4-terbutyl phenyl) 1-butanol and 100 g sodium carbonate in 100 ml ethanol are heated at reflux for 8 hours under stirring. After this set of time, the solvent is concentrated under reduced pressure. The dry residue is taken up after cooling with water to eliminate the mineral salts. The product is extracted with methylene chloride and after drying on sodium sulphate and after the solvent is eliminated in vacuum, the product is recrystallized from isopropyl ether to recover 27 g of pure compound as colourless crystals. Melting point 128.5°–131° C.

Step C: 1,3-dimethyl 7-(4-fluorobenzyl) 8-chloroxanthine

A solution of 43 g 1,3-dimethyl 8-chloro xanthine in 200 ml water and 20 ml sodium hydroxide 10N is heated to 70°–80° C., to which 27.6 ml 4-fluorobenzyl chloride are portion-wise added at this temperature within 4 hours. During this addition, 20 ml sodium hydroxide 10N are added by small portions to maintain the pH at an alkaline value. After achievement of this addition, the solution is further heated at 70°–80° for 2 hours then let to revert to room temperature under stirring. The precipitate is filtered, dried, washed with water until neutral, then dried. Thereafter it is recrystallized from acetone to recover 19 g of pure compound. It melts at 183°–184° C.

Step D: 1-4[(4-tertbutylphenyl) 4-hydroxy] 1-butyl 4-amino piperidine

A solution of 25.5 g of the oxime of step A in ethanol (previously dried on a molecular sieve 4A for a night), is reduced using metallic sodium at the reflux when all the metallic sodium has disappeared (23.5 g), boiling is maintained for 1 hour then the solution is cooled under nitrogen. A solution of 57 g ClH 4N in 200 ml water is added and ethanol is evaporated off at the maximum possible.

The thus-formed amine is extracted with n-butanol and after washing with water it is concentrated to dryness under vacuum. Its dry residue is taken up in methylene chloride, dried on sodium sulphate, filter and concentrated to dryness. The raw product is recrystallized from a mixture hexane (100 p)-methanol (1p)-13.3 g of the compound are thus-obtained. The derivative melts at 99.2° C.

Step E: 1,3-dimethyl 7-(4-fluorobenzyl) 8-[1-(4-tertbutyl phenyl) 4-hydroxybutyl-4 piperidyl)amino] Xanthine ($I_{A''}$)

A mixture of 32 g 8-chloro 7-(4-fluorobenzyl) theophylline, 16 g sodium iodide, 30 g 1-[(4-tertbutyl phenyl) 4-hydroxy] butyl-4 amino piperidine, 12 g sodium carbonate and 200 ml dimethyl formamide is heated at the reflux under nitrogen atmosphere for 24 hours.

After cooling, the suspension is poured into 800 ml iced water, the precipitate is filtered and dried, then washed until neutral. The raw product is purified by chromotography on alumina column, washing with hexane then with isopropyl ether and finally with acetone. After having concentrated the acetonic phase, 17.6 g of solid product are recovered which are further recrystallized from a mixture of hexane (3p) and acetone (1p). Melting point: 95° C.

| Analysis $C_{33}H_{43}N_6O_3F$ | | | |
|---|---|---|---|
| C | H | N | F% |
| Theoretical 67.09 | 7.3 | 14.22 | 3.22 |
| Found 67.10 | 7.27 | 14.03 | 3.18 |

UV (MeOH) $\chi$ max in nm: 296 and 216.2

IR (BrK) in cm$^{-1}$, 1224, 1625, 1640, 1605, 3330, 3400

NMR $^1$[H] Spectrum in CDCl$_3$: (internal ref. TMS, $\delta$ in ppm): 1.3 (s, 9H of tertbutyl) 3.38 (s, 3H of N—CH$_3$) 3.52 (s, 3H of N—CH$_3$) 4.60 (td, 1H, CH—O) 7–7.40 (m, 8H aromatics)

Hydrochloride: MP=167°–169°

Furmarate: MP=179°

EXAMPLE II

1,3-dimethyl 7-(4-fluorophenyl) 8-[4-(4-tertbutylphenyl) 4-hydroxybutyl)piperazinyl] Xanthine ($I_{A'}$)

Step A: 1-[(4-tertbutylphenyl) 4-hydroxyl] butyl piperazine 6.36 g piperazine as the anhydrous base are dissolved in 19 ml ethanol at 20° C. When the whole piperazine is dissolved, 8.90 g of 4-chloro 1-[4-(tertbutylphenyl)] 1-butanol are added at once.

The mixtures is heated at 80° C. for 6 hours then let to revert at 20° C. and the reaction mixture is extracted with isopropyl ether. The raw product is thereafter recrystallized from ethyl acetate. 6 g of pure compound are recovered. MP=114°–115° C.

Step B: 1,3-dimethyl 7-(4-fluorobenzyl) 8-[4-(4-tertbutylphenyl) 4-hydroxy)butyl piperazinyl] Xanthine A mixture of 16.53 g 7-(4-fluorobenzyl) 8-chloro theophylline and 14.86 g of 1-[4-(4-tertbutylphenyl) 4-hydroxy] butyl piperazine in 100 ml dry ethanol is prepared, then heated to 80° C. for 9 hours. After termination of the reaction, ethanol is concentrated under vacuum and the resulting product extracted with methylene chloride. After recrystallization in 1 vol ethanol and 2 vol isopropyl ether, 6 g of pure compound are recovered. MP=145° C.

| Analysis $C_{32}H_{41}N_6O_3F$ | | | |
|---|---|---|---|
| C | H | N | F% |
| Theoretical 66.63 | 7.11 | 14.57 | 3.29 |
| Found 66.24 | 7.08 | 14.53 | 3.65 |

UV (dry ethanol) $\chi$ max in nm=291.6 and 205.8

IR (KBr): $\nu$ cm$^{-1}$: 1222, 1440, 1510, 1660, 1700, 3180

NMR $^1$[H] (in CDCl$_3$, intern. Ref. TMS, $\delta$ in ppm): 1.3 (s, 9H of tertbutyl) 3.35 (s, 3H, N=CH$_3$) 3.52 (, 3H, N=CH$_3$) 4.65 (ex 1H, —CHO) 6.9–7.40 (m, 8H aromatics)

Hydrochloride: MP=202°–204° C.

Furmarate: MP=88°–89°

EXAMPLE III

1-(4-fluorobenzyl) 2-[4-(4-tertbutylphenyl) 4-hydroxybutyl)piperazino] benzimidazole ($I_B$)

Step A: 2-chlorobenzimidazole

A solution of 2-hydroxy benzimidazole (40.2 g) in 93 ml phosphorus oxychloride is heated to reflux under stirring for 6 hours. After achievement of the reaction the solution is let to revert to −10° C. and hydrolysed with 100 g crushed ice and 100 ml iced water. They are slowly added 249 ml sodium hydroxide 10N to get a neutral pH value. The precipitated product is filtered, washed with the minimal amount of water. The crystals are taken up in hot ethanol. After cooling, the alcoholic juice are filtered and concentrated to dryness.

Step B: 2-chloro 1-(4 fluorobenzyl) benzimidazole 11 g 2-chlorobenzimidazole are dissolved in 74 ml water and 17.35 ml 30% sodium hydroxide. The mixture is heated to 82° C. and to this they are slowly added 23.76 g 4-fluorobenzyl chloride within 5 hours. When the reaction is achieved, the solution is cooled to 20° C. and extracted with methylene chloride. The compound is recrystallized from ethyl acetate.

Step C; 1-(4-fluorobenzyl) 2-piperazinyl benzimidazole

In 168 ml xylene 40.8 g anhydrous piperazine and 60 g 2-chloro (4-fluorobenzyl) benzimidazole are added. The mixture is heated to 80° C. for 10 hours. When the reaction is no longer evoluting, the temperature is reverted to 20° C. and the pH value is adjusted to 2 with an aqueous solution of hydorchloric acid at 30%. The organic solution is washed with water then the pH is increased to pH 11 with sodium carbonate. The compound is extracted with isopropyl ether. Finally 46 g pure compound are recovered.

Step D: 1-(4-fluorobenzyl) 2-[4-(4-tertbutylphenyl) 4-hydroxybutyl) piperazino] benzimidazole In 80 ml n-butanol they are mixed 28.45 g 2-chloro 1-(4-fluorobenzyl) benzimidazole, 9.7 g sodium carbonate, 13.66 g sodium iodide and 30 g 4-chloro 1-(4-tertbutyl phenyl) 1-tetrahydropyranyloxy butane. The solution is heated to 100° C. for 16 hours. When the reaction is achieved, the compound is extracted with isopropyl ether; the organic phase is washed to neutral then concentrated to dryness. The alcoholic function is freed by hydrolysis with a solution of by hydrochloric acid at 0.6% for 45 mn. The compound is anew extracted with ether, neutralized with sodium carbonate and recrystallized from isopropyl ether with a minimal amount of ethanol. They are finally obtained 19.90 g of pure compound melting at 179.2° C.

| | Analysis $C_{33}H_{39}N_4OF$ | | | |
|---|---|---|---|---|
| | C | H | N | F% |
| Theoretical | 74.70 | 7.58 | 10.89 | 3.69 |
| Found | 73.57 | 7.73 | 10.71 | 3.66 |

UV (MeOH) χ max in nm: 285.6 and 248.8 213

IR (BrK) in $cm^{-1}$: 954, 1080, 1129, 1609, 3222

NMR $^1$[H] Spectrum in $CDCl_3$: (internal ref. TMS, δ in ppm): 1.3 (s, 9H of tertbutyl) 4.65 (td, 1H, —CHO) 5.15 (s, 2H, $CH_2$ benzylic) 6.9–7.65 (m, 12H aromatics)

Hydrochloride: MP=173°–175.5° C.

Fumarate: MP=196°–197°

EXAMPLE IV 1-(4-fluorobenzyl) 2-[4-(tertbutylphenyl) 4-hydroxybutyl) 4-piperidyl) amino] benzimidazole ($I_{B''}$)

Step A: 1-chloro (4-tertbutylphenyl) butanaol 200 g 1-chloro (4-tertbutylphenyl) 3-butanone are dissolved in 1680 ml methanol, then a solution of 16.78 g sodium borohydride in 151 ml water and 1.31 g sodium hydroxide are added thereto within 30 mn. The temperature of the reaction mixture is kept between 10° and 20° C. during addition of sodium borohydride. It is kept under stirring for 5 hours then the methanolic solution is concentrated under vacuum. The medium is extracted with isopropyl ether and the compound is recrystallized from 2 vol hexane. 183 g of pure compound are recovered. Its melting point is 50.9°–51.3° C.

Step B: 1-chloro 1-[4-tertbutylphenyl] 4-tetrahydropyranyloxy butane

In 8.7 ml dihydropyran they are added 10 mg p.toluene sulphonic acid (APTS). To this mixture they are added within 30 mn at 60°, 20 g 1-chloro (4-tertbutylphenyl) butanol. After this addition the mixture is still heated at between 60° and 65° C. for 30 mn and kept under stirring for further 90 mn. 0.5 g sodium bicarbonate is thereafter added. The mixture is then stirred for 1 hour. The tetrahydropyranylated derivative is directly used without any further purification.

Step C: N-(4-fluorobenzyl) phenylene diamine 56 g N-(4-fluorobenzyl) 2-nitroaniline are reduced in the presence of 34 g of 5% palladized charcoal into methanol (560 ml) using a stream of hydrogen at room temperature and normal pression. After achievement of the reaction, the mixture is washed with nitrogen, filtered on clay (Trade Mark Celite) and concentrated to dryness. The residue is recrystallized from isopropyl ether. The desired N-substituted phenylene diamine, is thus obtained recovered weight: 38.5 g. The starting material N-(4-fluorobenzyl) 2-nitroaniline is prepared by alkylating the 2-nitroaniline by means of 4-fluorobenzyl chloride in the methyl ethyl ketone.

Step D: 1-[(4-tertbutylphenyl) 4-tetrahydro pyranyloxybutyl] 4-hydroxyimino piperidine 58.4 g of 1-chloro 1-(4-tertbutylphenyl) 1-tetrahydro pyranyloxy butane in 200 ml ethanol are heated to reflux under stirring with 20 g 4-hydroxyimino piperidine and 20 g sodium carbonate. After 20 hours reflux, the solution is concentrated to dryness then taken up with water, extracted with dried methylene chloride and concentrated to dryness under vacuum 70.5 g of pure compound are thus produced. It is recrystallized from methanol to recover 40 g of a solid having a melting point of 150°–151° C.

Step E: 1-[(4-tertbutylphenyl) 4-tetrahydropyranyloxy butyl] 4-amino piperdine In a 1 l reactor, a solution of the corresponding oxime (35 g in 235 ml ethanol) is heated to reflux with 25.5 g sodium for reduction during 1 hour. After complete disappearance of the sodium the whole mixture is heated to reflux for ½ hour then cooled under nitrogen. They is introduced in the medium under stirring a solution of 60 g ammonium chloride in 250 ml water. It is extracted with isopropyl ether, the organic phase is washed with water, dried on sodium sulphate then concentrated to dryness. The residue is purified by recrystallization from methanol to eliminate the not yet reduced, optionally present oxime. The raw amine after concentration of the methanol, is purified by passing through a column filled with silica dispersed with hexane then eluted with methanol and the eluate is concentrated to dryness. 25 g of a compound are recovered as a thick oil.

Step F: 1-[(4-tertbutylphenyl) 4-tetrahydropyranyl oxybutyl)] isothiocyanatopiperidine In a 250 ml reactor they are put together 10 ml 10N sodium hydroxide and 50 ml water than after cooling to 5° C., they are added 6 ml carbon sulphide. A solution of 19.5 g of the amine of the preceding step E in 100 ml water and acetic acid is introduced thereto, within 1 hour between 0° and 20° C. and the pH value is adjusted to 7–8. The mixture is stirred for further 2 hours between 0° and 10° C. The disappearance of the amine is followed through TLC on silica in a mixture of $CHCl_3$/ethanol (7:3). The mixture is warmed to 20° C. and to the latter 10 ml ethyl chlorocarbonate are poured dropwise without passing 30° C. within ¾ hour. The whole mixture is heated for 2–3 hours at 50°–60° C. on the water-bath until cessation of the staining into brown, of a paper impregnated with lead acetate. (TLC on $SiO_2$ with cyclohexane 3-ethyl acetate 7). After cooling the solution is extracted with methylene chloride, washed, dried and concentrated to dryness. The product is purified on a column of silice dispersed with hexane and elution with a mixture of cyclohexane-5 ethyl acetate 5–15.3 g of a viscous product are thus obtained.

Step G: N-[1-(4-tertbutylphenyl) 5-tetrahydropyranyl) piperadinyl] oxybutyl]N-[2-(4-fluorobenzyl amino phenyl] Thio Urea In 150 ml methanol they are mixed 25.4 g 1-[4-tertbutylphenyl) 4-tetrahydropyranyl oxybutyl] 4-isocyanatopiperidine and 18.3 g N-(4-fluorobenzyl) 1,2-phenylene diamine and this mixture is kept aside for 24 hours. It is thereafter concentrated to dryness under vacuum and the residue is passed through a column filled with silica dispersed with cyclohexane, to eliminate the excess of aromatic amine. The resulting thiourea is extracted with ethyl acetate. 33 g of an oily compound are thus obtained.

Step H: 1-(4-fluorobenzyl) 2-4-tertbutylphenyl) 4-hydroxybutyl 4-piperidinyl amino] benzimidazole They are heated to reflux into 200 ml benzene, 33 g of the thiourea obtained in the step G, together with 16 g dicyclohexyl carbodiimide for 5 hours. After achievement of the reaction, it is cooled, washed with water than with an aqueous solution of sodium carbonate and further with water. It is dried and concentrated to dryness under vacuum, the residue is taken up with 100 ml methanol and 20 ml water, then the pH value is adjusted to 1 with concentrated hydrochloric acid. The end of the reaction is followed by TLC on silica plates with chloroform 7—ethanol 3 (revelation UV and Iodoplatinate). It is neutralized after dilution with water using sodium carbonate then sodium hydroxide to obtain a pH value of 12. It is extracted with methylene chloride, the organic solution is washed with water, dried, filtered and concentrated to dryness. 37 g of raw product are produced which are washed with isopropyl ether and 24 g of the pure compound are obtained. The product is recrystallized from ethyl acetate containing a little methanol. MP=164.8°165.2° C.

| | Analysis $C_{33}H_{41}N_4OF$ | | | |
|---|---|---|---|---|
| | C | H | N | F% |
| Theoretical | 74.96 | 7.82 | 10.60 | 3.59 |
| Found | 73.80 | 7.80 | 10.30 | 3.50 |

UV (MeOH) $\chi$ max in nm: 286.2–249.4 and 18.4

IR (BrK) in $cm^{-1}$: 1087, 1227, 1570, 1616, 3068, 3227

NMR $^1$[H] ($CDCl_3$, internal ref. TMS, δ in ppm): 1.3 (s, 9H of tertbutyl) 4.02 (td, 1H, —CHO) 5.03 (s, 2H, $CH_2$ benzylic) 6.90–7.55 (m, 12H aromatics)

Hydrochloride: 204°206° C.

Fumarate: 177°

EXAMPLE V

Examples of Realization of Pharmaceutical Formulations

| A - Soft gelatine capsules | |
|---|---|
| Active ingredient | 20 g |
| Lactose | 100 g |
| Microcrystalline Cellulose | 23 g |
| Magnesium stearate | 1 g |
| Colloidal silica | 1 g |
| enough for 1000 soft gelatine capsules | |
| B - Tablets | |
| Active ingredient | 50 g |
| Lactose for compression | 1360 g |
| Avicel PH 101 | 200 g |
| Precirol | 20 g |
| Colloidal silica | 20 g |
| enough for 10,000 tablets | |
| C - Drinkable solution | |
| Active ingredient | 150 mg |
| Preservative agents | 1 mg |
| Sorbitol (70% solution) | 50 g |
| Alcool at 95% | 20 g |
| Purified water enough for | 150 g |
| D - Injectible | |
| Active ingredient (in the form of a salt) as a base | 1 mg |
| Sodium chloride | 5 mg |
| Mono sodium phosphate enough for pH | 5.5–6 |
| purified water for injection enough, for | 5 ml |
| E - Suppositories | |
| Active ingredient | 2.5 mg |
| Whitepsol H35 and H37 (50:50) enough for | 3 g |
| F - Aerosols | |
| Active ingredient | 3% |
| Sorbitol trioleate | 2 to 2.5% |
| Propelling agent enough for | 100% |
| G - Eye drops | |
| Active ingredient in the form of its hydrochloride | 1 mg |
| Benzalkonium chloride | 0,00125 mg |
| purified water enough for | 5 ml |

PHARMACOLOGICAL STUDY OF THE COMPOUNDS ACCORDING TO THIS INVENTION

The pharmacological studies of the compounds according to this invention have included two aspects: characterization of the main activity of anti-histaminic H1 type and search of optional undesirable side-effects on the Central Nervous System (CNS). Each of these two sides could utilize as well "in vitro" techniques for measuring the affinity for specific receptors or studies on an isolated organ as models of "in vivo" pharmacological properties.

I—Characterization of the Anti H1 Activity 1.1 Measurement of the Affinity for the Receptors H1

Increasing concentrations of the compounds to be studied are incubated with membranar preparations of homogenates of rat cortexes or guinea pig lungs in the presence of a specific ligand of the H1 receptors: Mepyramine labelled with Tritium, at the fixed concentration 2 nM. After 30 mn at 25° C. and at pH 7.4, in a 50 mM TRIS-ClH buffer for the membrans of the cortex or a 0.5 M $PO_4HNa_2/PO_4H_2K$ buffer for the lungs membranes, the residual bound fraction of tritiated ligand is counted by scintillation in a liquid medium after filtration on an apparatur of the Brandel's type and several washings. The relationship between concentration of the compound to be studied and inhibition of the specific binding of tritiated Mepyramine to the H1 receptors, allows the calculation of the 50% inhibitory concentration ($CI_{50}$).

Under these experimental conditions, the compound of example III shows a $Cl_{50}$ of $1.1 \times 10^{-6}$ M on the H1 receptors of rat cortexes and $2.7 \times 10^{-6}$ M on the H1-receptors of guinea pigs lungs, against respectively $1 \times 10^{-6}$ M and $10^{-6}$ M of Terfenadine, a non-sedative anti-H1 active ingredient of reference (Woodward and Munro 1982). Both products then possess "in vitro" a very similar affinity for the H1 receptors in two different species.

1.2 Studies on Isolated Ileon of Guinea Pigs

Successive concentrations of the compounds to be studied are tested against the same range of increasing concentrations of histamine which act through its receptors of H1-type on the smooth muscular fibers from the wall of ileon, placed in a survival bath according to the technique detailedly described by FERRY and cowork (1970). The shift of the relationship between contracturing effect and concentration of histamine by the compound to be studied, stamps an anti-H1 activity. Under these experimental conditions, the compound of example III and Terfenadine behaves in a very similar manner: no effect at $10^{-7}$ M, inhibition of the competitive type (ie. which allows to refind the whole action of histamine at a higher concentration) at $10^{-6}$ M and partially irreversible inhibition (ie. antagonizing a portion of the contraction induced by Histamine whatever will be the concentration) at $10^{-5}$ M. If the compound of example III appears to be slightly more active than Terfenadine at $10^{-6}$ M, the opposite seems to be produced at $10^{-5}$ M without that any of these tinges be significative between both products.

1.3 Studies on the Bronchospasm to Histamine in the Guinea Pigs

Inhalating an aerosol at 1%, of histamine (aqeuous solution in distilled water, nebulization with a apparatus HOSPITAK) causes in the guinea pigs, a bronchospasm which leads with immobilization of the animals on their own side. The time needed for the animals to lie down is measured for 5 minutes maximum. This period is called time of resistance and will be longer when the animals have previously taken a compound endowed with anti H1-properties. Beyond the 300 seconds of observation, the animals are said to be "proteted" of the broncho-constrictive action of histamine (Olsson 1971).

Intraperitoneally a fast total protection of all the animals subjected to this test, has been obtained 30 minutes after administration of 10 mg/kg of Terfenadine or the compound of example III, their activity appear to be again very similar. At 1 and 3 m/kg, Terfenadine and the compound of example III remain poorly efficient under these experimental conditions. Within this range of dosages the regression curve allow the calculation of the efficient dosage at 50% ($ED_{50}$) for each of the compounds: about 6.7 mg/kg for the compound of example III and about 7 mg/kg for Terfenadine.

By oral way the single dosage of 10 mg/kg has been studied as a function of time. The guinea pigs which have been given this dosage of Terfenadine or of the compound of example III, are submitted to the test of Histamine aerosol from 30 mn, 1 hour, 2, 4, 6, 8, 12 and 24 hours after feeding (8 animals per product for each period). Terfenadine has only protected the animals for 4 hours whereas the animals which have received the compound of example III, have totally with stand to the effects of inhaled histamine until 12 hours after administration of the anti-H1 compound. At the time 24 hours, the total protection (for more than 5 minutes) can be still seen in 50% of the animals treated with the compound of example III, which shows then a more longer duration of action than that of Terfenadine.

Conclusively, compound of example III distinguishes one self among the compounds according to this invention as being carrier of a main anti-H1 action of same intrinsic potency as Terfenadine, ($CI_{50}$) on the H1 receptors, inhibition of the contraction of isolated ileon of guinea pig due to Histamine, $ED_{50}$ by intraperitoneal way against bronchospasm due to histamine in the guinea pigs but of higher duration of action after administration by oral way (bronchospasm due to Histamine in the guinea pigs).

II—Search of Optional Side-Effects on the Central Nervous System (CNS)

2.1 Measurements of Affinity for Various Receptors to Neuromediator

The compound of example III which has been selected on the basis of its leading antiH1 activity, has been compared to two other anti-H1 representatives of the two generations of this class of pharmacological agents. Mepyramine belongs to the first generation which displays residual sedative properties on the CNS. Terfenadine is the first representative of the second generation of anti-H1 compounds which is henceforth deprived of side effects on the SNC (GARRISON 1990).

A broad range of membranar receptors of various rats organs has been tested according to the same principle than the H1 receptor under the following conditions which are summarized:

Adenosine A1: cortex, 90 mn at 25° C. in 50 mM TRIS-ClH buffer (pH 7.7) against 1 nMol of [$^3$H] cyclohexyladenosine Adenosine A2: striatum 60 mn at 25° in 50 mM TRIS-ClH buffer (pH 7.7) added with 50 nM cyclopentyladenosine, 10 mM $Cl_2Mg$ and 0.1 Unit/ml adenosine-sesaminase against 4 nM of [$^3$H] NECA (5'-N-ethylcarboxamido adenosine).

Muscarinic M1: pool of cortex, striatum and hypocampus, 60 mn at 25° C. in 10 mM $PO_4HNa_2/PO_4H_2K$ buffer (pH 7.4) against 2 nM [$^3$H]-pirenzepine.

Muscarinic M2: pool of heart, ileon and cerebellus, 60 mn at 22° C. in 50 mM TRIS-ClH buffer (pH 7.5) against 0.5 nM of [$^3$H]QNB (quinuclindinyl benzylate).

Central sites to benzodiazepines: whole brain, 90 mn at 0° C. in 50 mM TRIS-ClH buffer (pH 7.1) against 0.3 nM [$^3$H]-Flunitrazepam.

Peripheral sites to the benzodiazepines: Cortex 90 mn at 25° C. in 90 mM $PO_4HNa_2/PO_4H_2K$ buffer, 81 mM ClNa and 9.5 nM ClK (pH 7.4) against 1 nM [$^3$H]PK 11195.

$GABA_A$: whole brain 20 mn at 4° C., in 50 nM TRIS-ClH buffer (pH 7.2) added to 0.5%. TRITON X-100, against 5 nM [$^3$H] Muscimol.

$GABA_B$: Cerebellum, 10 mn at 22° C. in 50 mM TRIS-ClH buffer (pH 7.4) added to 1.2 mM $SO^4Mg$ and 2.5 mM $Cl_2Ca$, against 20 nM of [$^3$H] Baclofen.

Sigma receptors: whole brain, 2 hours at 22° C. in 50 mM

TRIS-ClH buffer (pH 8) against 2 nM of [$^3$H] (+)3-PPP (3-(3-hydroxyphenyl)N-(1-propyl) piperidine).

As in the case of H1 receptor, the relationship between the percentages of inhibition of the specific binding of the tritiated ligand as a function of the increasing concentration of Mepyramine, Terfenadine or compound of example III, allows the calculation the $CI_{50}$ for each of the compounds for each of the receptors. The more weak is the $CI_{50}$, the more high is the affinity. When the inhibition is only partial, and does allow only the calculation of a theoretical $CI_{50}$ higher than $10^{-5}$ M, it may be considered that the affinity is very weak, indeed non existent.

The hereunder table summarizes the properties of the three studied H1-antihistaminics.

| $CI_{50}$ (M) | Mepyramine | Terfenadine | Compound of example III |
|---|---|---|---|
| Muscarinic $M_1$ | $3,8 \times 10^{-6}$ | $>10^{-5}$ | $>10^{-5}$ |
| Muscarinic $M_2$ | $3,5 \times 10^{-6}$ | $>10^{-5}$ | $>10^{-5}$ |
| Sigma receptor | $5,9 \times 10^{-7}$ | $>10^{-5}$ | $>10^{-5}$ |
| Sites to benzodiazepines: | | | |
| Central | $>10^{-5}$ | $>10^{-5}$ | $>10^{-5}$ |
| Peripheral | $>10^{-5}$ | $>10^{-5}$ | $>10^{-5}$ |
| Adenosine $A_1$ | $>10^{-5}$ | $>10^{-5}$ | $>10^{-5}$ |
| Adenosine $A_2$ | $>10^{-5}$ | $>10^{-5}$ | $>10^{-5}$ |
| $GABA_A$ | $>10^{-5}$ | $>10^{-5}$ | $>10^{-5}$ |
| $GABA_B$ | $>10^{-5}$ | $>10^{-5}$ | $>10^{-5}$ |

Mepyramine shows a moderate but real affinity for the muscarinic M1 and M2 sites, about 1000 times weaker than that of Atropin, the anticholinergic agent of reference. Moreover a non negectible affinity for the Sigma-receptor has been evidenced, of the order of 20 times weaker than that of pentazocine, the reference ligand for this receptor some of the effects of Mepyramine on the CNS may then found a functional basis in these residual non-H1affinities. At the contrary the absence of affinity which may be detected, under the same experimental conditions unit the compound of example III to Terfenadine.

2.2 Study on the Behaviour in the Mice

The Irwin's test, modified according to Morpurgo's Technique (1971) has been carried out to search optional alterations of the spontaneous behaviour under the action of the compound of example III or of a H1-antihistaminic of the first generation Dexchloropheniramine, known to induce some effects of drowsiness in the man. After administration by oral way, the mice have been kept under observation for 30 mn then have submitted to a seri. of simple test of behavioural screening after 30 mn, 3 hours and 24 hours.

Dexchlorpheniramine at a dosage of 100 mg/kg has induced a hyperactivity and a slight irritability of after 30 mn, persisting at 3 hours and disappearing after 24 hours. On the other side a mydriasis has been noticed after 3 hours. The compound of example III did merely induce a very weak passivity in half of the animals having received the maximal tested dosage of 400 mg/kg, at the time 3 hours only. Moreover in a search for a single maximal non-toxic dosage by the oral way in the same species, the mice which have received until 1000 mg/kg do not display any clinical symptom. This is less fine than the Irvin's Test during which the animals are handled and interact with the experimenter.

This lack of symptoms at high dosage is entirely of the opinion of an absence of effects on CNS. Hyperactivity due to dexchlorpheniramine does not correspond to the sedative effect encountered in the main but however found expression in an influence on the cns. The mydriasis results from an anticholinergic action at the ocular level, which is characteristic of Atropin by example.

2.3—Rota-Rod Test in the Mice

The principle of this test consists in chronometering the duration for which mice maintain itself on a rod rotating at a constant speed. Compounds which are endowed with sedative or myorelaxing or inhibitory of the motor coordination, will induce a precocious fall, before 120 seconds which are the maximals period of study. Beyond this time the animals considered as possessing intact psychomotor capacities (Andrasi and cowork 1982, Ongini and cowork 1987). This test takes place 30 mn and 60 mn after administration. By oral way the compound of example III did not alter the performances of the tested animals until the highest tested dosage of 100 mg/kg, in comparison with those recorded for mice, which receive only the vehicle of administration. Chlorpromazine, major neuroleptic used as positive standard in the Rota-rod Test, caused the fall before the time granted, of 90% of the mice from the dosage of 4 mg/kg by intraperitoneal way. In other supplemental assays, ketotifene fumarate—anti $H_1$ compound with long duration of action—has been shown to be able to decrease the performance of 25 to 35% of the treated mice with 50 mg/kg per oral way.

Conclusively compound of example III does not show noticeable effect on the CNS under experimental situations where other $H_1$ anti-histaminics lead to various neurological alterations, hyperactivity, irritability and mydriasis with dexchlorpheniramine, changes in the performances in the rota-rod test with ketotifene fumarate. Endly the profiles of affinity to the specific receptors of the main neurotransmitters allow a distinction between Mepyramine, antiH$_1$ of the first generation on one side and Terfenadine and the compound of example III on the other side. These latter compounds do not possess any residual affinity on the receptors, that let predict a profile similar to a non sedative type.

III—Conclusion of the Pharmacological Study

The compounds of this invention display at various degrees, anti-histaminic $H_1$ potentialities. Among them, the compound of example III presents a pharmacological profile, close to that of Terfenadine which is characterized with a strength of activity similar in vitro as well as in vivo and with a lack of side-effects on the CNS. Moreover the compound of example III possesses a duration of action higher than that of Terfenadine.

BIBLIOGRAPHICAL REFERENCES

ANDRAST F, BORVATH K, SINGER E, BERSENYL P, BORSY J, KENNESSEY A, TARR M, LANG T, KOROSI J and HAMORI T. Arzneim Forsch/Drug Res. 1987, 37:1119–1124

GARISSON J. C in "The Pharmacologic Basis of Therapeutics" 8 st. edi. by GILMAN A. G, RALL T. W, NIES A. S and TAYLOR P. Pergamon Press Inc., New York 1990, pp 575–588

MORPURGO C. Arzneim. Forsch/Drug Res. 1971, 11:1727–1734

OLSSON O. A. T Acta Allergologica, 1971, 26:438–453

PERRY and the members of Department of Pharmacology of the University of EDINBOURG in "Pharmacological experiments on isolated preparations" edited by E. S. LIVINGSTONE, EDINBOURG and LONDON, 1970: pp 58–87

WOODWARD J. K and MUNORO N. L Arzneim.Forsch/ Drug Res. 1982, 32:1154–1156

What is claimed is:

1. A compound selected from the group consisting of a (4-substituted phenyl) 4-oxy 1 aminobutane of the formula

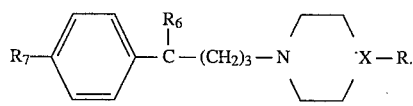

wherein $R_6$ is selected from the group consisting of

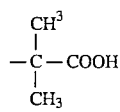

$R_7$ is selected from the group consisting of —COOH, tertbutyl and

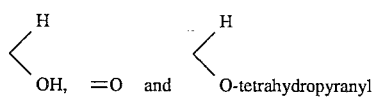

X is selected from the group consisting of >N— and >CH—NH and R is a cyclic substituent selected from the group consisting of a) a xanthic derivative of the formula

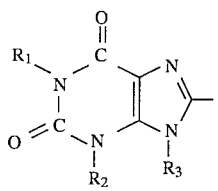

wherein $R_1$ and $R_2$ are individually selected from the group consisting of hydrogen and lower alkyl of 1 to 5 carbon atoms and $R_3$ is halobenzyl or ethoxyethyl and b) is benzimidazolic group of the formula

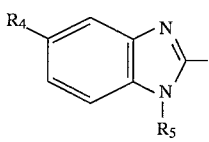

wherein $R_4$ is hydrogen or halogen and $R_5$ is halobenzyl or ethoxyethyl and their non-toxic, pharmaceutically acceptable acid addition salts.

2. A compound according to claim 1 having the formula $I_A$ wherein R is a xanthyl selected from the group consisting of piperazinyl xanthines of the formula

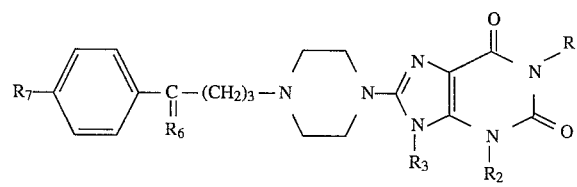

and the piperadyl amino xanthines of the formula

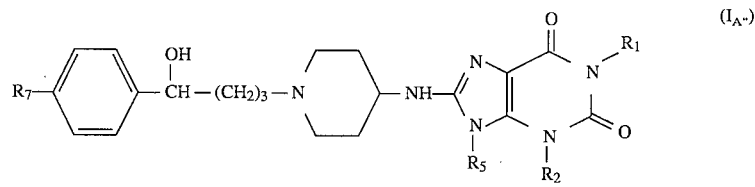

wherein $R_1$, $R_1'$ and $R_2$ are individually hydrogen or lower alkyl of 1 to 5 carbon atoms $R_3$ is halogenbenzyl group halobenzyl or ethoxyethyl and $R_4$ and $R_5$ are defined as in claim 1.

3. A compound according to claim 1 having the formula $I_B$ wherein R is a benzimidazolic radical, selected from the group consisting of piperazinyl benzimidazoles of formula $I_{B'}$

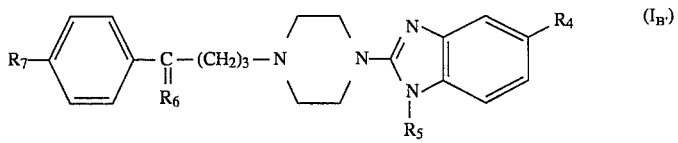

and the piperdylamino benzimidazoles of formula $I_{B''}$

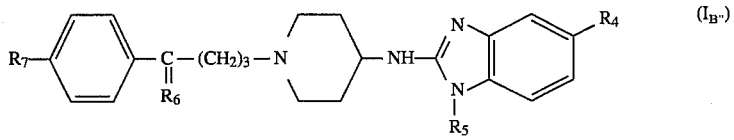

wherein $R_4$, $R_5$, $R_6$ and $R_7$ have the definitions of claim 1.

4. The acid addition salts of compound of formula I according to claim 1 with a mineral or organic acid.

5. The optically-active isomers of a compound of formula I according to claim 1.

6. The compounds of formula I' according to claim 1

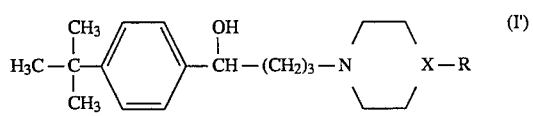

wherein X and R are defined as defined in claim 1.

7. The compounds according to claim 1 having the formula $I_A$

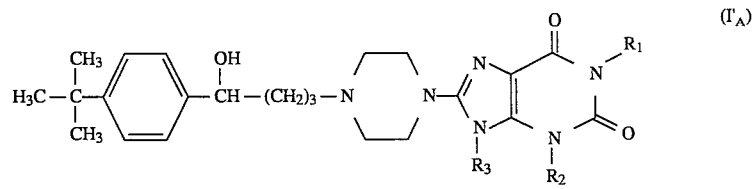

wherein $R_1$ and $R_2$ have the definitions of claim 1.

8. A compound according to claim 1 having the formula $I'_B$

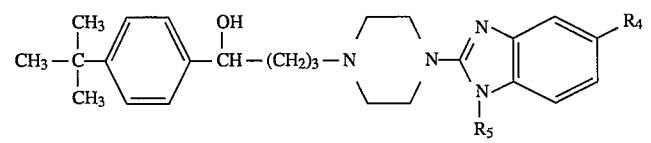

wherein $R_4$ and $R_5$ have the definitions of claim 1.

9. A compound according to claim 1 which is 1,3-dimethyl 7-(4-fluorobenzyl) 8-[1-(4-tertbutylphenyl 4-hydroxy) butyl piperidyl-4 amino] xanthine.

10. The compounds according to claim 1 which is 1,3-dimethyl 7-(4-fluorobenzyl) 8-[4-(4-tertbutylphenyl 4-hydroxybutyl) piperzinyl] xanthine.

11. The compounds according to claim 1 which is 1-[4-fluorobenzyl) 2-[4-(4-tertbutylphenyl) 4-hydroxybutyl] piperazino benzimidazole.

12. The compounds according to claim 1 which is (1-(4-fluorobenzyl) 2[(4-tertbutylphenyl 4-hydroxybutyl-4) piperidyl-4 amino] benzimidazole.

13. A method of inducing anti-histamine H1 activity in warm-blooded animals comprising administering to said warm-blooded animals in need thereof an effective anti-histamine H1 activity inducing amount of a compound of claim 1.

* * * * *